US011007160B2

(12) United States Patent
Fraser et al.

(10) Patent No.: US 11,007,160 B2
(45) Date of Patent: May 18, 2021

(54) METHOD OF VIRAL INHIBITION

(71) Applicant: Monash University, Clayton (AU)

(72) Inventors: Johanna Elisabeth Fraser, Warranwood (AU); David Andrew Jans, Caulfield South (AU); Kylie Michelle Wagstaff, Cockatoo (AU)

(73) Assignee: Monash University, Clayton (AU)

( * ) Notice: Subject to any disclaimer, the term of this patent is extended or adjusted under 35 U.S.C. 154(b) by 0 days.

(21) Appl. No.: 14/785,059

(22) PCT Filed: Apr. 16, 2014

(86) PCT No.: PCT/AU2014/050017
§ 371 (c)(1),
(2) Date: Oct. 16, 2015

(87) PCT Pub. No.: WO2014/169355
PCT Pub. Date: Oct. 23, 2014

(65) Prior Publication Data
US 2016/0074346 A1    Mar. 17, 2016

(30) Foreign Application Priority Data

Apr. 16, 2013  (AU) ................................ 2013901525

(51) Int. Cl.
*A61K 31/167*    (2006.01)
*A61K 31/203*    (2006.01)
(52) U.S. Cl.
CPC .......... *A61K 31/167* (2013.01); *A61K 31/203* (2013.01); *Y02A 50/30* (2018.01)
(58) Field of Classification Search
CPC ..... A61K 31/203; A61K 31/167; A61P 31/14; Y02A 50/30

USPC .................................................. 514/559, 613
See application file for complete search history.

(56) References Cited

U.S. PATENT DOCUMENTS

| 7,169,813 | B2 * | 1/2007 | Formelli ................. A61P 43/00 514/563 |
| 8,993,744 | B2 * | 3/2015 | Ross ...................... A61K 39/12 536/23.72 |
| 9,090,911 | B2 * | 7/2015 | O'Neill .................. C12N 15/01 |
| 10,294,280 | B2 * | 5/2019 | Coulibaly ............ C07K 14/005 |

(Continued)

FOREIGN PATENT DOCUMENTS

| WO | 2009114136 | 9/2009 |
| WO | 2014169355 | 10/2014 |

OTHER PUBLICATIONS

Johansen et al. (AN2008:352859,DN 148:394354, abstract of WO 2008033466).*

(Continued)

*Primary Examiner* — Sabiha N Qazi
(74) *Attorney, Agent, or Firm* — Chris Marion; Stephanie M. Greer; Lauren L. Stevens

(57) ABSTRACT

This invention relates to methods of treating or preventing viral infections caused by flaviviruses, such as dengue virus, yellow fever virus, West Nile virus or Japanese encephalitis virus or infections caused by Chikungunya virus (CHIKV). The methods involve the administration of retinoic acid analogues to subjects who have, are suspected of having a flavivirus infection or infection with CHIKV, or to those who are at risk of becoming infected with a flavivirus or becoming infected with CHIKV.

8 Claims, 9 Drawing Sheets

(56) References Cited

U.S. PATENT DOCUMENTS

| | | | |
|---|---|---|---|
| 10,406,127 B2* | 9/2019 | Betancourt | A61K 9/4866 |
| 10,512,619 B2* | 12/2019 | Betancourt | A61K 9/1652 |
| 2003/0171339 A1 | 9/2003 | Sin | |
| 2006/0264514 A1 | 11/2006 | Formelli | |
| 2008/0161324 A1* | 7/2008 | Johansen | A61K 31/135 |
| | | | 514/255.03 |
| 2008/0261978 A1* | 10/2008 | Clark | C07C 237/30 |
| | | | 514/235.8 |
| 2015/0272976 A1* | 10/2015 | Padmanabhan | A61K 31/519 |
| | | | 514/25 |

OTHER PUBLICATIONS

Finnegan et al. (PNAS, Oct. 2004, vol. 101, No. 60, pp. 15452-15457).*

June Su Yin Low et al. (Antiviral Therapy 2011; 16:1203-1218).*

Caly, L. et al., Nuclear Trafficking of Proteins From RNA Viruses: Potential Target for Antivirals? Antiviral Research, 2012, 95: 202-206.

Clyde, K. et al., Recent Advances in Deciphering Viral and Host Determinants of Dengue Virus Replication and Pathogenesis, J Viral, 2006, 80(23): 11418-11431.

Formelli, F. et al., Pharmacokinetics of Oral Fenretinide in Neuroblastoma Patients: Indications for Optimal Dose and Dosing Schedule Also With Respect to the Active Metabolite 4-oxo-fenretinide, Cancer Chemother Pharmacol, 2008, 62: 655-665.

Green, S. et al., Immunopathological Mechanisms in Dengue and Dengue Hemorrhagic Fever, Current Opinion in Infectious Diseases, 2006, 19: 429-436.

Medin, C L et al., Dengue Virus Nonstructural Protein NS5 Induces Interleukin-8 Transcription and Secretion, J Viral, 2005, 79(17): 11053-11061.

Paradkar, P N et al., Unfolded Protein Response (UPR) Gene Expression During Antibody-Dependent Enhanced Infection of Cultured Monocytes Correlates with Dengue Disease Severity, Biosci Rep, 2011, 31: 221-230.

Pryor, M J et al., Nuclear Localization of Dengue Virus Nonstructural Protein 5 Through Its Importin $\alpha/\beta$-Recognized Nuclear Localization Sequences is Integral to Viral Infection, Traffic, 2007, 8(7): 795-807.

Wati, S. et al., Dengue Virus (DV) Replication in Monocyte-Derived Macrophages Is Not Affected by Tumor Necrosis Factor Alpha (TNF-alpha), and DV Infection Induces Altered Responsiveness to TNF-alpha Stimulation, J Virol, 2007, 81(18): 10161-10171.

Zellweger, R M et al., Antibodies Enhance Infection of LSECs in a Model of ADE-Induced Severe Dengue Disease, Cell Host Microbe, 2010, 7(2): 128-139.

Aktepe, T. et al., Differential Utilisation of Ceramide During Replication of the Flaviviruses West Nile and Dengue Virus, Virology, 2015, 484: 241-250.

Carocci, M. et al., The Bioactive Lipid 4-Hydroxyphenyl Retinamide Inhibits Flavivirus Replication, Antimicrobial Agents and Chemotherapy, 2015, 59(1): 85-95.

Finnegan, C. et al., Fenretinide Inhibits HIV Infection by Promoting Viral Endocytosis, Antiviral Research, 2006, 69: 116-123.

Fraser, J. et al., A Nuclear Transport Inhibitor That Modulates the Unfolded Protein Response and Provides In Vivo Protection Against Lethal Dengue Virus Infection, Journal of Infectious Diseases, 2014, 210: 1780-1791.

International Application No. PCT/AU2014/050017; International Preliminary Report on Patentability, dated Oct. 10, 2015, 4 pages.

International Application No. PCT/AU2014/050017; International Search Report and Written Opinion of the International Searching Authority dated Oct. 10, 2014, 7 pages.

Low et al., Narasin, A Novel Antiviral Compound That Blocks Dengue Virus Protein Expression, Antiviral Therapy, 2011, 16: 1203-1218.

Miyake et al., Serine Palmitoyltransferase is the Primary Target of a Sphingosine-Like Immunosuppressant, ISP-1/Myriocin, Biochemical and Biophysical Research Communications, 1995, 211(2): 396-403.

Rahmaniyan, M. et al., Identification of Dihydroceramide Desaturase as a Direct In Vitro Target for Fenretinide, Journal of Biological Chemistry, 2011, 286(28): 24754-24764.

* cited by examiner

FIG. 9A  FIG. 9B

METHOD OF VIRAL INHIBITION

RELATED APPLICATIONS

This application is a US National stage entry of International Application No. PCT/AU2014/050017, which designated the United States and was filed on Apr. 16, 2014, published in English. This application claims priority under 35 U.S.C. § 119 or 365 to Australian Application No. 2013901525, filed on Apr. 16, 2013. The entire teachings of the above applications are incorporated herein by reference.

FIELD OF THE INVENTION

This invention relates to a method of treating viral infections caused by flaviviruses, such as dengue virus, yellow fever virus, West Nile virus or Japanese encephalitis virus. In particular, it relates to methods and compounds for treating dengue virus infection, including prevention of infection by dengue virus.

BACKGROUND OF THE INVENTION

Arbovirus is a term used to refer to a group of viruses that are transmitted by arthropod vectors such as mosquitoes and ticks. Flaviviruses are among those transmitted in this way, and include West Nile virus, dengue virus, tick-borne encephalitis virus, and yellow fever virus. Of these, dengue virus is considered one of the most significant arboviruses, with an estimated 390 million cases of dengue fever occurring worldwide. The alphavirus Chikungunya virus (CHIKV) is another example of an arbovirus. Most of these infections are in tropical areas of the world.

Like many of the flavivirus infections, symptoms of having been infected with dengue virus include sudden high fever, severe headaches, pain behind the eyes, a rash, severe joint and muscle pain, nausea and vomiting and mild bleeding. In more severe cases, infected individuals may develop dengue hemorrhagic fever, a rare complication characterized by more severe bleeding, damage to lymph and blood vessels, enlargement of the liver, and failure of the circulatory system, all of which can in turn lead to shock and death.

Currently infections are treated symptomatically as there is no licensed vaccine or effective anti-viral. Moreover dengue fever is caused by one of five closely related, but antigenically distinct, virus serotypes (DENV-1, DENV-2, DENV-3, DENV-4 and a recently identified single isolate DENV-5), and infection with one serotype may not protect a subject from infection with a different serotype.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

Infections from flaviviruses such as dengue virus serotypes 1-4 (DENV1-4), West Nile virus (WNV) and Japanese encephalitis virus (JEV) account for as many as 200,000 deaths/year worldwide. Although DENV infections have increased globally in the last 50 years, with now >40% of the world's population estimated to be at risk, there is no efficacious vaccine or anti-viral therapeutic currently available to combat DENV.

CHIKV infection causes an illness with an acute febrile phase lasting two to five days, followed by a longer period of joint pains in the extremities. The pain associated with CHIKV infection of the joints may persist for weeks or months, or in some cases years especially in the elderly. Like many arbovirus infections, there is no specific treatment aimed at clearing the virus.

Using a high throughput assay to screen for compounds that interfere with specific protein-protein interactions, the inventors have identified a retinoic acid analogue and structurally related retinoic acid analogues that have efficacy in the treatment or prevention of flaviviruses, and in particular the treatment or prevention of dengue fever, caused by DENV. These "anti-DENV agents" are effective against all 4 circulating serotypes of DENV (DENV1-4) and can be used either prophylactically to protect individuals in DENV-infested regions, or as efficacious therapeutics post-infection.

Accordingly, in a first aspect of the invention, there is provided a method of treating flavivirus infection, preferably dengue virus (DENV) infection, comprising administering an effective amount of a retinoic acid analogue to a subject in need thereof. Typically the amount administered achieves a therapeutically effective level in the subject. In an alternative embodiment of this aspect of the invention, the flavivirus infection treated is infection caused by yellow fever virus (YFV), WNV, or JEV.

It is also envisaged that subjects having CHIKV infection will benefit from administration of an effective amount of the retinoic acid analogue of the invention.

The words "treat" or "treatment" refer to therapeutic treatment wherein the object is to slow down (lessen) an undesired physiological change or disorder. For the purposes of this invention, beneficial or desired clinical results include, but are not limited to alleviation of symptoms of dengue virus infection and stabilised (i.e., not worsening or progressing) dengue virus infection.

The phrase "effective amount" or "therapeutically effective level" and similar terms means an amount of the retinoic acid analogue such as N-(4-hydroxyphenyl) retinamide (4-HPR) that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, or (v) reverses damage caused prior to treatment to some extent. The reversal does not have to be absolute. The amount administered may be higher than what is required within the body to achieve the therapeutic effect, but takes in to account the absorption, distribution, metabolism and excretion (ADME) profile of the analogue, the route of administration and the administration frequency.

In an alternative embodiment, the severity of symptoms associated with flavivirus infection in a subject, preferably DENV infection, can be reduced by administering a therapeutically effective amount of a retinoic acid analogue to the subject. As explained above in the context of treatment, by "reducing symptom severity" it is meant that one or more symptoms are attenuated, ameliorated, or eliminated, or the onset of one or more symptoms is prevented or delayed.

Symptom severity may also be reduced in a subject infected with CHIKV.

In a subject suspected of having flavivirus, or a subject with symptoms of being infected with a flavivirus such as DENV, YFV, WNV, or JEV, a diagnostic or confirmation test may be conducted either prior to or after the commencement of retinoic acid analogue administration.

In another aspect of the invention there is provided a method of preventing flavivirus infection, comprising administering an effective amount of a retinoic acid analogue to a subject in need thereof. Typically, the amount administered achieves a prophylactically effective level in the subject, thereby preventing flavivirus infection.

In an alternative embodiment of the invention, there is provided a method of preventing CHIKV infection, comprising administering an effective amount of a retinoic acid analogue to a subject in need thereof. Typically, the amount administered achieves a prophylactically effective level in the subject, thereby preventing CHIKV infection.

By "an effective amount" or similar terms, in the context of preventing infection it is meant the amount of retinoic acid analogue administered that is sufficient to achieve a prophylactically effective level wherein that level protects the subject from becoming infected with a flavivirus, preferably DENV, YFV, WNV or JEV, and most preferably DENV. The amount administered may be higher than what is required within the body to achieve the preventive/prophylactic effect, but takes in to account the ADME profile of the analogue, the route of administration and the administration frequency.

In preferred embodiments, the flavivirus is DENV, and may be one or more of serotypes 1, 2, 3 and 4.

In a further embodiment of the invention, there is provided a method for preventing antibody dependent enhanced (ADE) DENV infection, comprising administering an effective amount of a retinoic acid analogue to a subject in need thereof. Typically the amount administered achieves a therapeutically effective level in the subject to reduce the risk of ADE DENV infection. The subject will have had a prior DENV infection with a different DENV serotype.

The retinoic acid analogue is preferably N-(4-hydroxyphenyl) retinamide (4-HPR), also known as Fenretinide. 4-HPR may be formulated as a composition for treatment, or as a composition for prevention. In an alternative embodiment, 4-HPR metabolites may be administered. One preferred metabolite is N-(4-hydroxyphenyl)-4-oxoretinamide (4-oxo-4-HPR). In yet a further embodiment, the retinoic acid analogue is a 4-HPR variant according to Formula I, as described herein. Each of 4-HPR, a 4-HPR metabolite or a 4-HPR variant may be administered alone as the only active ingredients, or combinations thereof. When administered in combinations, preferably the compounds work synergistically. All embodiments are contemplated by the invention.

A "therapeutic composition", "pharmaceutical composition", "composition for treating" or "prophylactic" and other like terms refers to a composition including a retinoic acid analogue such as 4-HPR, combined with appropriate, pharmaceutically acceptable salts, carriers or diluents.

By "co-administration", it is meant that the 4-HPR and/or its metabolites and/or 4-HPR variants as described herein may be formulated as a single composition, administered as separate compositions contemporaneously, or administered consecutively as separate compositions. Co-administration can also refer to the administration of the retinoic acid analogue with a second therapeutic agent, such as pain relievers, to help alleviate the symptoms of infection.

The retinoic acid analogues of the invention may also be prepared as a medicament for the treatment of flavivirus infection, to reduce symptom severity in a subject having or suspected of having a flavivirus infection, for the prevention of infection by a flavivirus, or for the prevention of ADE DENV infection.

In an alternative embodiment, the retinoic acid analogues of the invention may also be prepared as a medicament for the treatment of CHIKV infection, to reduce symptom severity in a subject having or suspected of having CHIKV infection or for the prevention of infection by CHIKV.

There is also provided a retinoic acid analogue or a composition thereof when used to treat flavivirus infection, reduce symptom severity in a subject having or suspected of having a flavivirus infection, prevent infection by a flavivirus, or prevent ADE DENV infection.

The invention further provides for a retinoic acid analogue or a composition thereof for treating flavivirus infection, reducing symptom severity in a subject having or suspected of having a flavivirus infection, preventing infection by a flavivirus, or preventing ADE DENV infection.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

FIGS. 9A-9C. 4-HPR is effective against the arboviruses CHIKV (FIG. 9A and FIG. 9B) and WNV (FIG. 9C).

DETAILED DESCRIPTION OF THE EMBODIMENTS

Figure 1A:
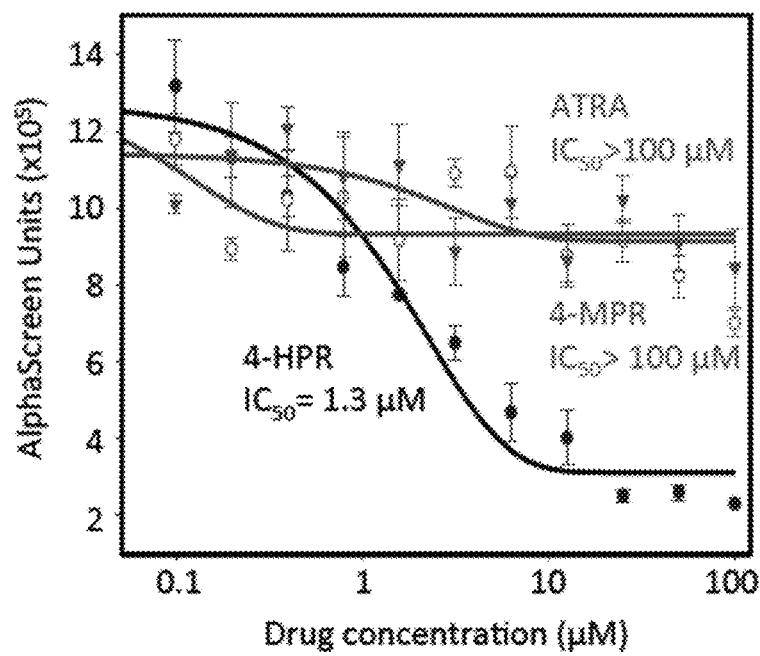
FIGS. 1A-1B. 4-HPR (FIG. 1A) and 4-oxo-4-HPR (FIG. 1B) can specifically block association of DENV-2 NS5 with IMPα/β1.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Dengue virus (DENV) is a mosquito-borne single positive-stranded RNA virus of the family Flaviviridae, within the genus flavivirus. There are 5 antigenically distinct virus serotypes; the four circulating serotypes DENV-1, DENV-2, DENV-3, and DENV-4, and the recently identified single isolate DENV-5, each of which is able to cause symptomatic infection in humans. Its genome codes for three structural proteins—capsid protein (C), membrane protein (M) and envelope protein (E)—and seven nonstructural proteins—NS1, NS2a, NS2b, NS3, NS4a, NS4b, NS5.

Despite there being a good understanding of the DENV structure and lifecycle, efforts by others in the field prior to the current invention have failed to develop an effective vaccine or anti-viral therapy for humans infected with DENV. Inhibitors targeted exclusively at host cell proteins are problematic in that targeting host proteins often results in toxicity, while agents directed at viral components result in viral resistance (Caly et al. 2012). In contrast, targeting host cell:viral protein interfaces represents a viable strategy to derive antivirals that do not kill normal cells or select for virus resistance. The identification by the inventors of a retinoid capable of inhibiting dengue virus by targeting host cell:viral protein interactions therefore represents a novel and viable treatment for dengue infection. Moreover, the retinoid identified is able to reduce infection when added prior to, as well as post-infection, indicating it could be efficacious both prophylactically and as a therapeutic.

Treatment and/or prevention (prophylaxis) is aimed at one or more of, without limitation:
i) reducing viral load in a subject infected with a flavivirus including but not limited to DENV, YFV, WNV, or JEV, and in particular, a person infected with any serotype of DENV.
ii) reducing or ameliorating the risk to a subject of infection with a flavivirus including but not limited to DENV, YFV, WNV, or JEV, and in particular, the risk of infection with any one or more serotypes of DENV.
iii) alleviating symptoms of a flavivirus infection in a subject, having or suspected of having a flavivirus infection including but not limited to DENV, YFV, WNV, or JEV, and particularly DENV infection.
iv) reducing or ameliorating the risk of antibody dependent enhanced (ADE) DENV infection in a subject having had or suspected of having had a previous DENV infection.

In alternative embodiments of the invention, each of (i) to (iii) is applicable to CHIKV.

Accordingly, in one aspect of the invention, there is provided a method of treating flavivirus infection, preferably DENV, YFV, WNV, or JEV infection and most preferably DENV, comprising administering an effective amount of a retinoic acid analogue to a subject in need thereof. Typically the amount administered achieves a therapeutically effective level in the subject.

There is also provided a use of an effective amount of a retinoic acid analogue in the preparation of a medicament for treating flavivirus infection, preferably DENV, YFV, WNV, or JEV infection and most preferably DENV, in a subject in need thereof. The retinoic acid analogue is preferably 4-HPR, or one or more 4-HPR metabolites, or 4-HPR and one or more 4-HPR metabolites.

Retinoids are a class of natural and synthetic vitamin A-derivatives in which the terminal carboxyl group of retinoic acid is linked to an aminophenol residue. In a particularly preferred embodiment of the invention, the retinoic acid analogue is N-(4-hydroxyphenyl) retinamide (4-HPR), also known commercially as "Fenretinide". Fenretinide is known to be clinically well tolerated and there is substantial interest in its use for clinical trials in various cancers, including neuroblastoma and breast cancer. Due to its low toxicity and effect on various pathways including ceramide biosynthesis, free radical oxygen and nitric oxide synthase, 4-HPR has also been investigated as a preventative and therapeutic agent in various diseases such as diabetes, HIV infection, Alzheimers Disease, cystic fibrosis, allergic encephalomyelitis, ichthyosis and ophthalmic conditions. It has not however been known to have any therapeutic effects on flaviviruses such as DENV.

In a preferred embodiment of the invention, there is provided a method of treating flavivirus infection, preferably DENV, YFV, WNV, or JEV infection and most preferably DENV, comprising administering an effective amount of a retinoic acid analogue to a subject in need thereof, wherein the amount administered achieves a therapeutically effective level in the subject, wherein the retinoic acid analogue administered is N-(4-hydroxyphenyl) retinamide.

4-HPR may be administered as a single active, formulated as a composition for treatment, or as a composition for prevention. 4-HPR may be metabolised once administered to the subject to produce therapeutically effective metabolites. The metabolites may themselves also be administered and be effective at treating or preventing flavivirus infections, such as DENV infection. For example, N-(4-hydroxyphenyl)-4-oxoretinamide (4-oxo-4-HPR). Accordingly, in another embodiment of the invention, there is provided a method of treating flavivirus infection, preferably DENV, YFV, WNV, or JEV infection and most preferably DENV, comprising administering an effective amount of a retinoic acid analogue to a subject in need thereof, wherein the amount administered achieves a therapeutically effective level in the subject, and wherein the retinoic acid analogue administered is N-(4-hydroxyphenyl)-4-oxoretinamide.

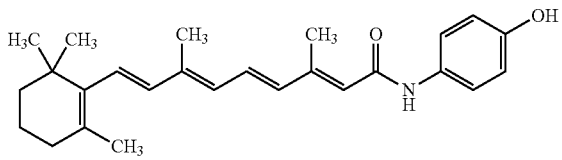

N-(4-hydroxyphenyl) retinamide (4-HPR; Fenretinide)

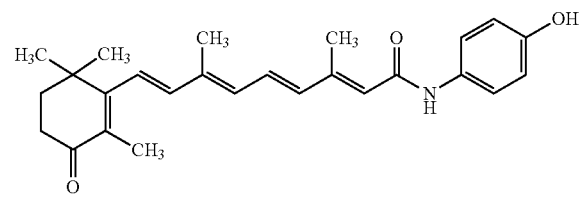

N-(4-hydroxyphenyl)-4-oxoretinamide (4-oxo-4-HPR; 3-Keto Fenretinide)

Alternatively, the metabolites of 4-HPR may be co-administered with 4-HPR and preferably work synergistically with the 4-HPR. Co-administration includes formulation of 4-HPR and one or more metabolites as a single composition, administered as separate compositions contemporaneously, or consecutive administration of separate compositions.

In an alternative embodiment, the retinoic acid analogue is a compound according to the following Formula I:

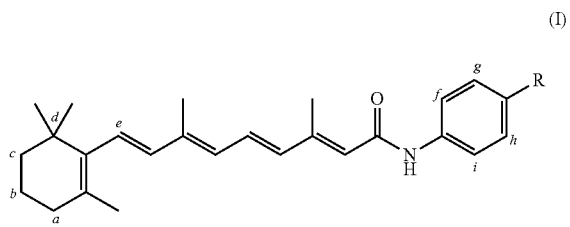

(I)

wherein:
R is OH, COOH, CH$_2$OH, CH$_2$CH$_2$OH, or CH$_2$COOH;
carbons a-d and f-i are optionally substituted with one or more groups selected from CH$_3$, OH, COOH, (CH$_3$)$_2$ and CH$_2$OH, or any combination thereof, and
carbon e is optionally substituted with a C$_1$-C$_3$ alkyl group that is optionally substituted with CH$_3$ and/or OH.

For the purposes of this invention, these compounds are collectively referred to as 4-HPR variants.

Without wishing to be bound by any theory as to the mechanism of action, the inventors have shown that 4-HPR acts by inhibiting the association of DENV non-structural protein 5 (NS5) protein with host cell importin proteins, and thereby blocks NS5 nuclear localisation. NS5 provides RNA-dependent RNA polymerase activity, enabling the virus to copy itself. Despite the fact that DENV replication occurs entirely within the cell cytoplasm, replication is highly dependent on the nuclear localisation of NS5 in the host cell nucleus (Pryor et al., 2007, Traffic). The inventors were the first to show that NS5 trafficking into and out of the nucleus is dependent on interaction with specific host cell nuclear transport receptors, and that these could therefore represent viable antiviral targets. In order for NS5 to enter the nucleus it must traffic through nuclear pore complexes embedded in the nuclear envelope. This is controlled by the binding of NS5 via its nuclear localisation signals (NLS) to its specific nuclear transport proteins, the importins (IMP) $\alpha/\beta 1$ (and particularly IMP$\alpha$) which in turn is critical for subsequent modulation of specific gene transcription relating to modulation of the host immune response (IL-8 production and inhibition of cell cycle progression) required for efficient virus production. The NLS is conserved across DENV1-4 serotypes, making this invention advantageous in that it is effective for all circulating DENV serotypes. The NLS is also conserved across other flaviviruses such as YFV and JEV.

Accordingly, in another aspect of the invention, there is provided a method of blocking NS5 nuclear localisation, comprising administering an effective amount of a retinoic acid analogue to a subject, preferably the retinoic acid analogue is 4-HPR and/or one of more metabolites of 4-HPR and/or one or more 4-HPR variants according to Formula I. Typically an effective amount of a retinoic acid analogue to block NS5 nuclear localisation is an amount of retinoic acid analogue that minimises or prohibits binding of NS5 to IMP$\alpha/\beta 1$ and particularly to IMP$\alpha$, thereby reducing the ability of NS5 to get in to the nucleus.

4-HPR has previously been reported to inhibit dihydroceramide desaturase and thereby de novo ceramide synthesis. Replication of the dengue-related virus, JEV, has been shown to be dependent on ceramide; DENV replication is also tightly linked to lipid synthesis although a role for ceramide has not been examined. It is possible that inhibition of ceramide synthesis is another mechanism of action for 4-HPR inhibition of virus replication, such as DENV replication.

Another possible mechanism of action relates to cell stress responses. 4-HPR has been studied for its anti-tumour and chemo-preventative properties where it specifically induces apoptosis in cancerous cells. Interestingly, the inventors have shown that addition of 4-HPR to DENV-infected cells induces activation of the pro-apoptotic PERK pathway within the unfolded protein response (UPR), but does not result in cell death at concentrations that effectively remove the virus. Without being bound by any theory, activation of the PERK pathway may facilitate host responses against DENV and also $WNV_{KUN}$, with specific activation of the PERK arm of the UPR leading to a potent antiviral state.

In any of the treatment methods of the invention, the retinoic acid analogue administered may consist only of 4-HPR, 4-oxo-4-HPR, or a 4-HPR variant according to Formula I, or two or more of 4-HPR, 4-oxo-4-HPR and a 4-HPR variant according to Formula I as the only active ingredients.

Alternatively, the patient may also be receiving other treatments, such that the 4-HPR or compositions thereof are administered in an adjunct therapy. Additional therapies may be those that treat the accompanying symptoms including, without limitation, pain relief such as aspirin, acetaminophen and codeine, and nonsteroidal anti-inflammatory drugs (NSAIDS). In this regard, there is provided a method of treating flavivirus infection, or a method of reducing symptom severity in a patient having or suspected of having a flavivirus infection, comprising administering an effective amount of a retinoic acid analogue to a subject in need thereof, together with another therapeutic, wherein the amount of retinoic acid analogue administered achieves a therapeutically effective level in the subject.

In a preferred embodiment, the flavivirus is one or more serotypes of DENV, the retinoic acid analogue administered is 4-HPR and/or one or more 4-HPR metabolites and/or 4-HPR variants according to Formula I, and the additional therapeutic is one or more of pain relief such as aspirin, acetaminophen and codeine, and NSAIDS.

Symptoms may also be reduced in a patient infected with or suspected of being infected with CHIKV by administration of a retinoic acid analogue of the invention.

In the treatment methods of the invention described herein, the methods may further include the step of diagnosing the subject. Diagnosis may be conducted before administration of the retinoic acid analogue, or after administration. Diagnosis may be made on the basis of:

symptoms qRT-PCR serological assays including, but not limited to ELISA and RIA.

While infection by one DENV serotype is protective of re-infection by the same serotype, the subject may not be protected by infection with other serotypes. Subsequent infection with a different serotype is thought to result in ADE DENV infection. Accordingly, in some embodiments of the invention, the subject has had a prior DENV infection with a different DENV serotype. These subjects are at higher risk of ADE DENV infection. The methods of the invention are also suitable for preventing ADE DENV infection.

ADE occurs when circulating antibodies from a previous infection with a different DENV serotype lead to increased viral load, caused by cross-reactive but non-neutralising antibodies. It also results in the increased expression of genes such as those encoding the cytokines interleukin (IL) 8 and tumor necrosis factor (TNF) and in turn, the development of the more severe manifestations of DENV infection of dengue haemorrhagic fever (DHF)/dengue shock syndrome (DSS) (Medin et al., 2005, J Virol.; Wati et al., 2010, J Gen Virol.; Green and Rothman, 2006, Curr Opin Infect Dis.; Clyde K et al. 2006, J Virol.). Little is known of the mechanisms behind ADE, but recent data from the inventors indicates a mechanistic link to DENV NS5 (unpublished observations).

Accordingly, in a further embodiment of the invention, there is provided a method for preventing ADE DENV infection, comprising administering an effective amount of a retinoic acid analogue to a subject in need thereof. Typically the amount administered achieves a therapeutically effective level in the subject to reduce the risk of ADE DENV infection. The retinoic acid analogue is preferably 4-HPR, a 4-HPR metabolite such as 4-oxo-4-HPR, or a 4-HPR variant according to Formula I or optionally 2 or more of 4-HPR, a 4-HPR metabolite and a 4-HPR variant according to Formula I.

There is also provided a use of an effective amount of a retinoic acid analogue in the preparation of a medicament for preventing ADE DENV infection in a subject in need thereof. The retinoic acid analogue is preferably 4-HPR, optionally with one or more 4-HPR metabolites, or a metabolite itself, such as 4-oxo-4-HPR. The retinoic acid analogue may alternatively be a 4-HPR variant according to Formula I on its own, or in combination with one or more of 4-HPR and a 4-HPR metabolite, such as 4-oxo-4-HPR.

The inventors have shown that not only is 4-HPR able to reduce DENV when added to cells infected with DENV, but that treatment of cells with 4-HPR prior to exposing those cells to DENV protected the cells. Accordingly, in another aspect of the invention, there is provided a method of preventing flavivirus infection, preferably DENV, YFV, WNV, or JEV infection and most preferably DENV, comprising administering an effective amount of a retinoic acid analogue to a subject in need thereof, wherein the amount administered achieves a prophylactically effective level in the subject, thereby preventing flavivirus infection.

In an alternative embodiment, there is provided a method of preventing CHIKV infection, comprising administering an effective amount of a retinoic acid analogue to a subject in need thereof, wherein the amount administered achieves a prophylactically effective level in the subject, thereby preventing CHIKV infection.

There is also provided a use of an effective amount of a retinoic acid analogue in the preparation of a medicament for preventing flavivirus infection, preferably DENV, YFV, WNV, or JEV infection and most preferably DENV, in a subject in need thereof. The retinoic acid analogue is preferably 4-HPR, or one or more 4-HPR metabolites, or one or more 4-HPR variants or 4-HPR, two or more of 4-HPR metabolites and 4-HPR variants according to Formula I.

A medicament may also be prepared for preventing CHIKV infection.

The effective amount can be determined using methods known in the art and by the methods described in the examples section of the specification.

In any of the prophylactic and therapeutic methods of the invention, the retinoic acid analogue administered may consist of 4-HPR, 4-oxo-4-HPR, a 4-HPR variant of Formula I or two or more of 4-HPR, 4-oxo-4-HPR and 4-HPR variants as the only active ingredients.

The retinoic acid analogues for use in the methods of the invention can be formulated as pharmaceutical compositions by combination with appropriate, pharmaceutically acceptable carriers or diluents. For convenience, the compositions will be described in greater detail with reference to the preferred retinoic acid analogue, 4-HPR. However, as has been detailed throughout the specification, the retinoic acid analogue administered may also be a metabolite of 4-HPR, such as 4-oxo-4-HPR. It may alternatively be a 4-HPR variant according to Formula I.

In pharmaceutical dosage forms, the 4-HPR may be administered alone or, as already mentioned above, in association or combination with other pharmaceutically active compounds such as NSAIDS and pain relievers to help treat the associated symptoms of DENV, YFV, WNV, or JEV infection. Those with skill in the art will appreciate readily that effective dose levels for 4-HPR will vary as a function of the nature of the delivery vehicle, the metabolism of the compound, the mode of delivery, the frequency of administration and the like. As noted above, these are all factors taken in to consideration when determining the amount to be administered in order to achieve therapeutic or prophylactic levels.

Pharmaceutically acceptable carriers or diluents contemplated by the invention include any diluents, carriers, excipients, and stabilizers that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as plasma albumin, gelatine, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In general the formulations are prepared by uniformly and intimately bringing into association the active ingredient with liquid carriers or finely divided solid carriers or both, and if necessary, shaping the product. Formulation may be conducted by mixing at ambient temperature at the appropriate pH, and at the desired degree of purity, with physiologically acceptable carriers, i.e., carriers that are non-toxic to recipients at the dosages and concentrations employed.

4-HPR is preferably formulated into preparations for oral delivery with the Lym-X-Sorb® (Lymphatic Xenobiotic AbSorbability) drug delivery system with controlled release (BioMolecular Products, Inc.). The 4-HPR is complexed in a 1:1 molar ratio with the Lym-X-Sorb, forming stable particles 10 to 70 nm in size, which are readily absorbed in the presence of sodium bicarbonate and bile salt. The 4-HPR complex is therefore better protected from digestive degradation (biomolecularproducts.com website).

In the treatment methods of the invention the 4-HPR compositions are administered to an infected human subject in need of treatment for a certain period of time. That period of time can vary on the type of viral infection, the severity of the viral infection, the stage of infection, and the responsiveness of the subject to treatment. In general, the subject will be treated for a period of 5 to 14 days. Upon completing treatment, the subject can optionally be tested for the presence of virus to confirm the success of treatment.

In the case of treating a subject to prevent them from becoming infected with, for example, DENV, the subject may take a daily dose of 4-HPR for as long as they are at risk of becoming infected with DENV. For example, for subjects going to locations endemic for DENV, the subject will take the 4-HPR for the entire period they are in the location. Preferably, administration will begin 1 to 5 days prior to arriving in the location, and will continue for 1 to 14 days after leaving the location.

The dose to be administered, for either treatment or prophylaxis, may be in the form of single doses of higher concentration, or divided doses of lower concentration. The concentration of any given dose will depend on the frequency of administration.

In another embodiment there is provided a kit or article of manufacture including a retinoic acid analogue, preferably 4-HPR, or pharmaceutical composition as described above.

In other embodiments there is provided a kit for use in a therapeutic application mentioned above, the kit including:
 a container holding the retinoic acid analogue, preferably 4-HPR, or pharmaceutical composition thereof; and
 a label or package insert with instructions for use in the methods of the invention described herein.

In certain embodiments the kit may contain one or more further active principles or ingredients for treatment of DENV, YFV, WNV, or JEV infections as described above.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a retinoic acid analogue, preferably 4-HPR, or pharmaceutical composition thereof which is effective for treating the condition and may have a sterile access port (for example the container may be an intravenous solution bag or a vial having a stopper pierceable by a hypodermic injection needle). The label or package insert indicates that the retinoic acid analogue, preferably 4-HPR, or pharmaceutical composition thereof is used for treating the condition of choice. In one embodiment, the label or package insert includes instructions for use and indicates that the retinoic acid analogue, preferably 4-HPR, or pharmaceutical composition thereof can be used to treat or prevent the methods described above.

Further aspects of the present invention and further embodiments of the aspects described in the preceding paragraphs will become apparent from the following description, given by way of example and with reference to the accompanying drawings.

EXAMPLES

Example 1

Effect of Retinoic Acid Analogues on NS5-IMPα/β1 Association

To investigate the structure/activity relationship for 4-HPR and 4-oxo-4-HPR, all-trans retinoic acid (ATRA; the parent compound of 4-HPR) and N-(4-methoxyphenyl) retinamide (4-MPR; a closely related analogue of 4-HPR) were compared in their ability to inhibit association of NS5 with IMPα/β1:

4-HPR; N-(4-hydroxyphenyl) retinamide

4-MPR; N-(4-methoxyphenyl) retinamide

ATRA; All trans retinoic acid 4-oxo-4-HPR; N-(4-hydroxyphenyl)-4-oxoretinamide

Figure 1B:
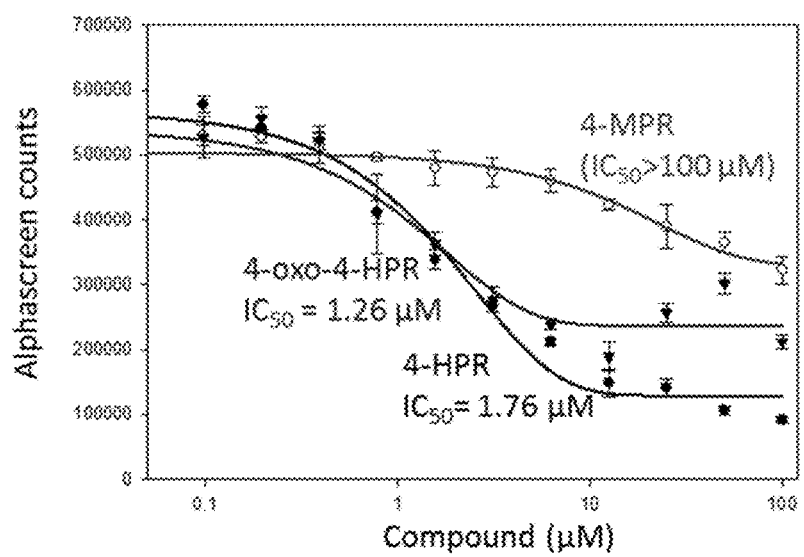

ALPHASCREEN®, a luminescent bead-based assay that measures direct protein-protein interactions, was used to examine the binding of 3 nM His$_6$-NS5 to 10 nM IMPα/β1 (IMPα/β1 heterodimer containing biotinylated IMPβ1) in the presence of increasing concentrations of 4-HPR, 4-MPR or ATRA (FIG. 1A), or 4-oxo-4-HPR, 4-HPR or 4-MPR (FIG. 1B). Data are the mean+standard deviation (SD) of triplicate wells from a single typical experiment.

4-HPR and 4-oxo-4-HPR were the only retinoic acid analogues able to block association of DENV-2 NS5 with IMPα/β1 (FIG. 1A and FIG. 1B). In contrast to 4-HPR and 4-oxo-4-HPR, neither ATRA nor 4-MPR were able to disrupt association of these proteins, underlining the specificity of the interaction.

Example 2

Specific Inhibition of DENV-2 NS5 Association with IMPα

To investigate the specificity of 4-HPR inhibition of NS5-importin association, the binding of 30 nM His$_6$-NS5 to 10 nM IMPα/β1, (IMPα/β1 heterodimer containing biotinylated IMPβ1), 3 nM IMPαΔIBB (biotinylated IMPα with the IMPβ-binding domain removed), or 3 nM biotinylated IMPβ1, in the presence of increasing concentrations of 4-HPR, was investigated. 4-HPR was found to interfere with association of NS5 and IMPα/β1, as well as NS5 and IMPαΔIBB (a truncated form of IMPα which lacks the auto-inhibitory IMPβ-binding domain), with 50% inhibition of binding occurring at similar concentrations (average IC$_{50}$ of 1.2 and 1.6 μM, respectively, from 3 independent experiments; representative assay shown), while NS5 binding to IMPβ1 alone was largely unaffected by the presence of 4-HPR.

Figure 2:
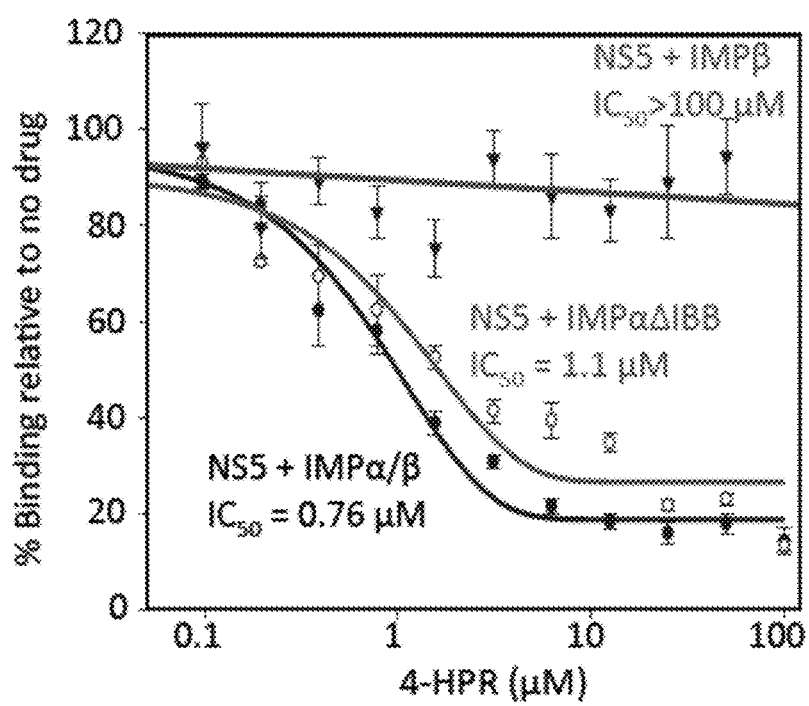
FIG. 2. 4-HPR can specifically block association of DENV-2 NS5 and IMP IMPα/β1, but not DENV-2 NS5 and IMPβ1.

These further investigations determined that 4-HPR prevents NS5 from binding to the NLS binding site on IMPα in vitro, by targeting either or both NS5 and IMPα (FIG. 2).

Example 3

4-HPR Antiviral Specificity

Figure 3A:
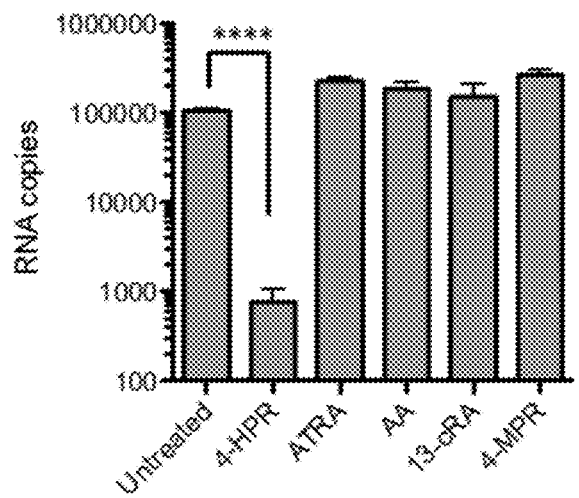
FIGS. 3A-3B. The anti-DENV activity of 4-HPR (FIG. 3A) and 4-oxo-4-HPR (FIG. 3B) is highly specific and not a general activity of retinoic acid analogues.
Figure 3B:
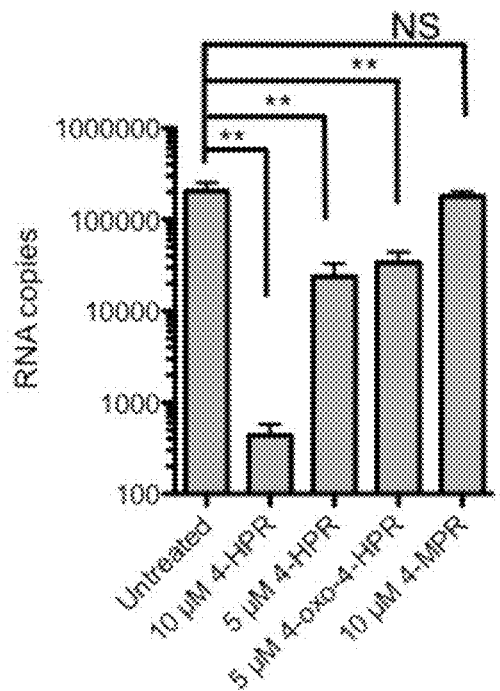

To test the specificity of 4-HPR and 4-oxo-4-HPR for anti-DENV activity Vero cells were infected with DENV-2 with a multiplicity of infection (MOI) of 1, in the presence of drug diluent (untreated) or the indicated compounds (10 µM in FIG. 3A, or 10 µM or 50 µM as indicated in FIG. 3B) for 2 h, followed by removal of the virus/drug inoculums, and addition of fresh 2% FCS maintenance medium. At 24 h post infection (p.i.) the culture medium was collected and the viral RNA extracted using QIAamp viral RNA mini kit (Qiagen). Absolute RNA copies present in each sample were determined by Taqman One Step RT-PCR (Applied Biosystems), as an estimate of virus titre by extrapolation from a standard curve generated from in vitro transcribed DENV RNA. Data shown are the mean+standard error of the mean (SEM) for 3 (FIG. 3A) or 2 (FIG. 3B) independent experiments. Statistical analysis (Student's t test) was performed using GraphPad Prism software. 4-HPR was found to have potent antiviral activity in this context, with 10 µM of the compound causing a 2-log reduction in viral RNA copies at 24 h p.i. (**$p<0.0001$) (FIG. 3A). 4-oxo-4-HPR was also found to have significant antiviral activity, with 5 µM treatment causing a 1-log reduction in viral RNA copies at 24 h p.i ($p<0.01$), similar to 5 µM 4-HPR (FIG. 3B). By contrast, addition of 10 µM ATRA, 4-MPR, or 2 other 4-HPR analogues, arotinoid acid (AA) and 13-cis retinoic acid (13-cRA), had no effect on DENV infection (FIG. 3A; NS, not significant).

Example 4

Toxicity Analysis

To determine the effect of 4-HPR on cell viability, and to ensure that the reduced viral titres were not due to compound toxicity, XTT reagent was used to measure mitochondrial activity of drug treated cells. Briefly, Vero cells were incubated with 0, 1, 10 or 25 µM 4-HPR for 24 h. XTT reagent was added directly to cells and incubated for 6 h at 37° C. prior to spectrophotometric analysis. Data shown are the mean+SD of a single experiment performed in triplicate wells.

Figure 4:
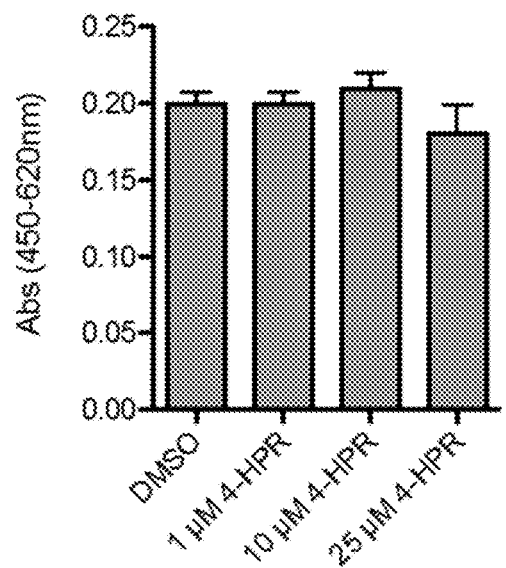
FIG. 4. 4-HPR has a highly favourable toxicity profile.

Treatment of Vero cells for 24 h with up to 25 µM 4-HPR had no effect on cell viability (FIG. 4). This is indicative of a highly favourable toxicity profile for 4-HPR and confirms the previous favourable toxicity profiles seen where 4-HPR has been used to treat various cancers, including in children, at concentrations of up to 4,000 mg/m²/day, administered daily for 28 days (Formelli et al., 2008, Clin, Cancer Chemother Pharmacol).

Example 5

4-HPR as a Prophylactic and Treatment for Dengue Virus Infections

To investigate whether 4-HPR can inhibit DENV-2 replication when added prior to infection or post infection (p.i.), 10 µM drug or DMSO (drug diluent) was added to Vero cells 2 h prior to infection, for 2 h during infection, 2 h p.i., or 24 h p.i. In each instance the drug was incubated with the cells for 2 h then removed. Infections were performed for 2 h (MOI of 1) followed by analysis of intracellular viral RNA by qRT-PCR 48 h p.i. Data shown are the mean+SD from one experiment, representative of three independent assays.

Figure 5A:
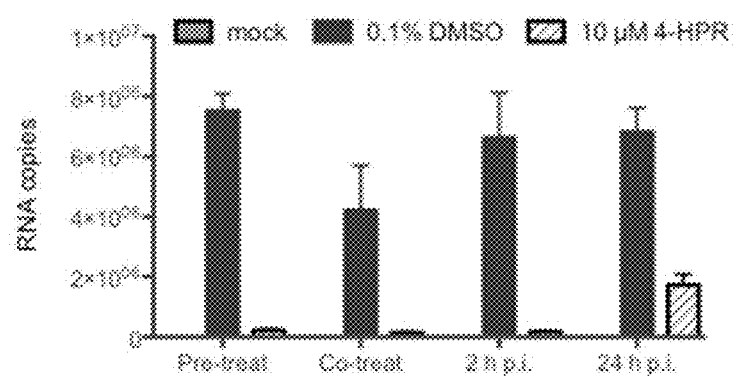
FIGS. 5A-5C. 4-HPR blocks DENV replication when applied to cells prior to (FIG. 5A) and after infection (A, B, C).

Treatment of cells with 4-HPR prior to, during, or up to 24 h p.i caused a substantial reduction of intracellular DENV-2 RNA copies (FIG. 5A). This suggests that 4-HPR can have prophylactic activity to protect against infection, as well as being effective when added p.i. as an infection treatment.

Figure 5B:
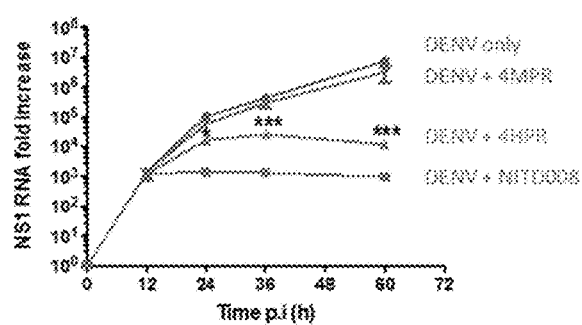

To gain further insight into the mode of action of 4-HPR, the human liver carcinoma cell line, Huh-7 cells were infected with DENV-2 (MOI of 1), followed by delayed addition of drug diluent DMSO (DENV only), 7.5 µM 4-HPR, 7.5 µM 4-MPR or 10 µM NITD008 (a previously described adenosine nucleoside inhibitor), 12 h post infection. Cells were lysed at the indicated times, RNA was extracted by Trizol and analysed by qPCR with fold change in expression of NS 1 calculated relative to the untreated control (FIG. 5B). Concurrently, culture medium was collected and viral titres determined by plaque assay (FIG. 5C).

In the untreated DENV control, or infected cells treated with 7.5 µM 4-MPR, viral RNA levels increased steadily until 60 h p.i. (FIG. 5B). In contrast, addition of 7.5 µM 4-HPR to Huh-7 cells at 12 h p.i. resulted in significantly reduced viral RNA levels relative to the infection control and 4-MPR-treated cells, with a 1-log reduction observed within 12 h (24 h p.i., *$p<0.05$). Interestingly, the amount of viral RNA present did not increase between 24 h and 60 h p.i. This result was comparable to the reduced RNA levels obtained in infected cells treated with the polymerase inhibitor NITD008 (***$p<0.005$).

Figure 5C:
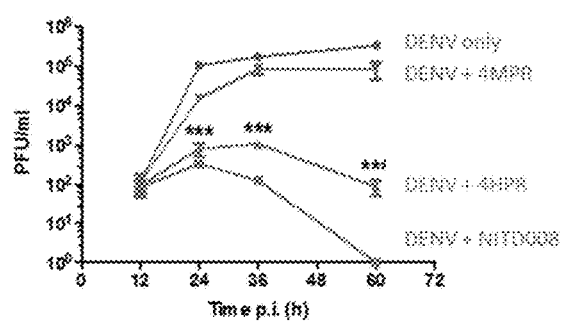

Parallel analysis of the amount of infectious virus produced revealed results consistent with reduced RNA levels, where delayed addition of 4-HPR resulted in significantly reduced virus titres over the 60 h infection period, relative to the untreated and 4-MPR controls (***$p<0.001$, FIG. 5C). A maximal reduction was reached at 60 h p.i. where the virus titre was 3-logs lower in 4-HPR-treated cells compared to the untreated and 4-MPR-treated controls, showing similar reductions to the NITD008 control. This finding has implications for the potential therapeutic use of this compound, suggesting that the compound may be efficacious in treating an established infection.

Example 6

4-HPR Blocks Replication of all Four Circulating DENV Serotypes

There are 4 circulating serotypes of DENV, and infection with one serotype is not protective of infection with another. It is therefore important that any prophylactic or treatment is effective against each serotype.

Figure 6A:
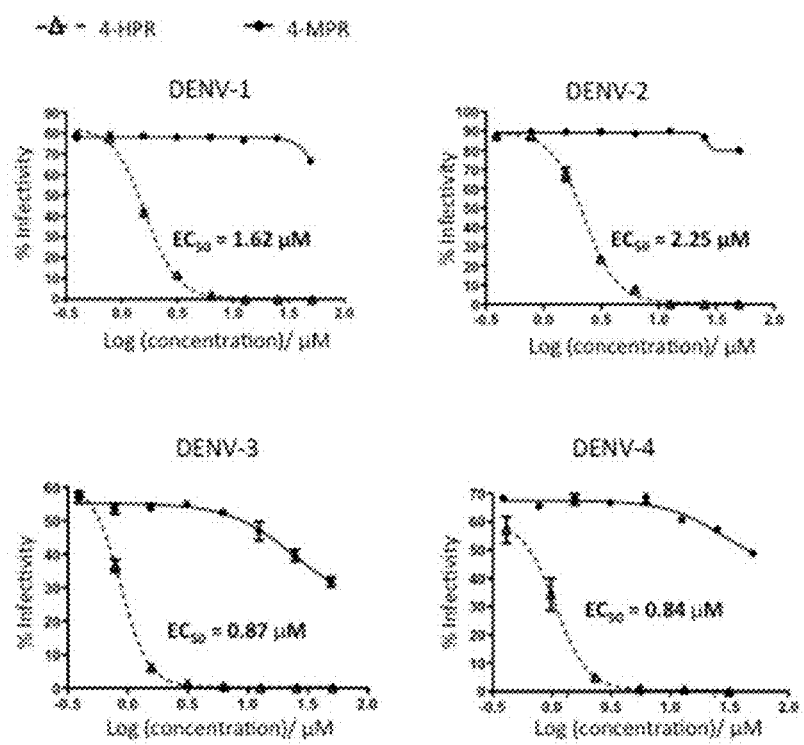
FIGS. 6A-6B. 4-HPR specifically blocks replication of DENV serotypes 1-4 in the BHK-21 cell line (FIG. 6A) and Huh-7 cell line (FIG. 6B).

To investigate this, BHK-21 cells were infected with DENV serotypes 1, 2, 3 or 4 (MOI of 0.3) for 1 h in the presence of 4-HPR or 4-MPR (concentrations as indicated in FIG. 6A). Virus inoculum was removed and fresh media containing the indicated compounds was added. Virus infection rates were determined 48 h p.i. using a cell-based flavivirus immunodetection assay. Briefly, cells were fixed and stained for DENV structural protein, E, followed by addition of Alexa Fluor 488 anti-mouse IgG. Viral antigen quantification was performed using Imagexpress. Data shown are representative of a single experiment.

4-HPR was found to block replication of all 4 DENV serotypes in BHK-21 cells with a low $EC_{50}$. DENV-4 was found to be inhibited with the lowest $EC_{50}$ (0.84 µM) while DENV-2 was inhibited with the highest $EC_{50}$ (2.24 µM). Consistent with the previous findings for DENV-2, it was found that 4-MPR did not have any effect on the replication of DENV serotypes 1, 2, 3, or 4. These findings demonstrate that 4-HPR is similarly effective against all circulating DENV serotypes.

Figure 6B:
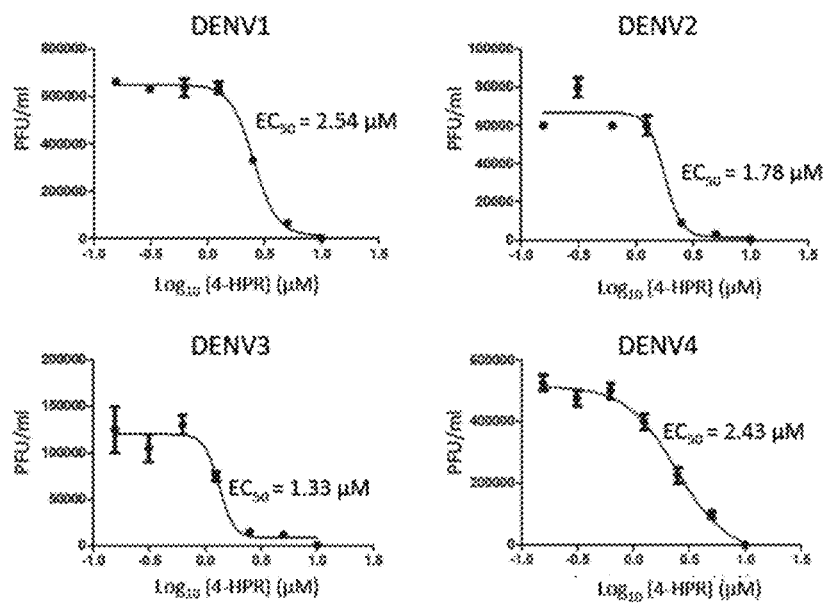

To ensure the antiviral activity of 4-HPR is not cell-line specific Huh-7 cells were also infected with DENV-1, 2, 3 or 4 (MOI of 0.3) in the presence of increasing concentrations of 4-HPR, with infectious virus titres determined by plaque assay at 48 h p.i. All 4 serotypes of DENV were restricted with similar $EC_{50}$ values (average of 2.6, 2.1, 1.4 and 2.1 µM for DENV 1, 2, 3 and 4, respectively, from 2 independent experiments; see FIG. 6B, representative data shown), consistent with the findings in BHK-21 cells.

Example 7

4-HPR is Effective Against DENV-1/Antibody-Dependent Enhanced Infection

In a cell culture model of antibody-dependent enhanced (ADE) DENV infection, THP-1 human monocyte cells infected with DENV-1 in the presence of sub-neutralising levels of a humanized version of the 4G2 antibody, which is cross-reactive with flavivirus envelope proteins (Paradkar et al., 2010 Bio Sci Rep.), show increased virus production compared to cells infected with virus alone. This model mimics the ADE phenomenon thought to occur in patients infected with a second serotype of DENV, which is associated with more severe DENV disease.

Figure 7:
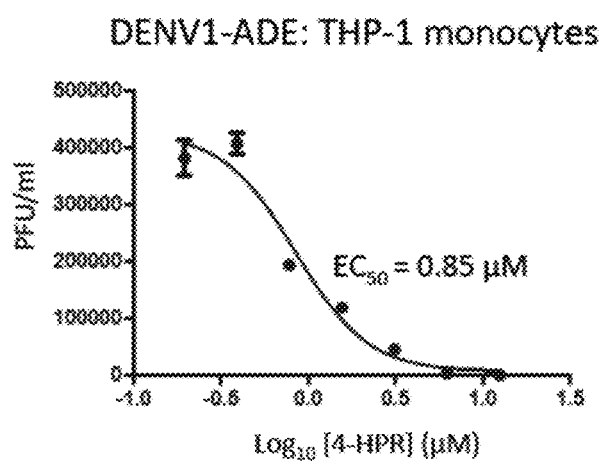
FIG. 7. 4-HPR is effective against DENV-1/antibody-dependent enhanced infection.

Briefly, humanized 4G2 antibody (0.05 µg/ml) was combined with DENV-1 (MOI of 10), and 4-HPR (concentrations as indicated in FIG. 7) in serum-free media, and incubated on ice for 1 h for the immune complex to form. Immune complex inoculums were added to THP-1 cells and incubated for 48 h. Supernatants were collected after 2 days and infectious virus production was quantified by plaque assay.

4-HPR was highly effective in blocking ADE-mediated DENV-1 infection in THP-1 cells (FIG. 7). A low $EC_{50}$ of 0.85 µM was determined. This finding indicates that 4-HPR is effective in restricting DENV replication, even when infection occurs via ADE, which is considered to be linked to more severe disease outcomes.

Example 8

4-HPR Provides Protection Against DENV Infection Ex Vivo and In Vivo

The antiviral activity of 4-HPR was investigated in the more physiologically relevant human system of peripheral blood mononuclear cells (PBMCs), a major target of DENV infection in humans.

Figure 8A:
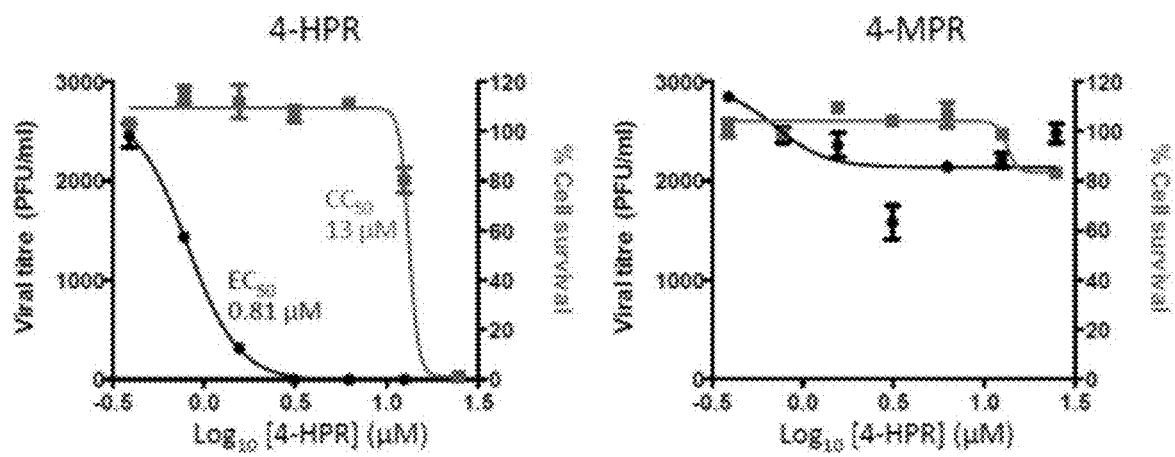
FIGS. 8A-8C. 4-HPR is able to protect against DENV infection in PBMCs (FIG. 8A) and in a lethal infection mouse model (FIG. 8B and FIG. 8C).

PBMCs were prepared from a healthy donor buffy coat using a Ficoll gradient, prior to ADE-mediated DENV-1 infection (MOI of 10) in the presence of increasing concentrations of 4-HPR or 4-MPR, and infectious virus titres determined by plaque assay 48 h later. In this system 4-HPR was determined to be highly effective with an ex vivo $EC_{50}$ value of 0.81 µM (FIG. 8A, viral titre is plotted on the left hand y-axis, black line), in contrast to no reduction in infected PBMCs treated with 4-MPR. Cytotoxicity analysis of 4-HPR in this system indicated a $CC_{50}$ value of >13 µM (FIG. 8A, cell survival is plotted on the right hand y-axis, grey line), underlining the fact that the loss of infectious virus is not due to induction of cell death.

Figure 8B:
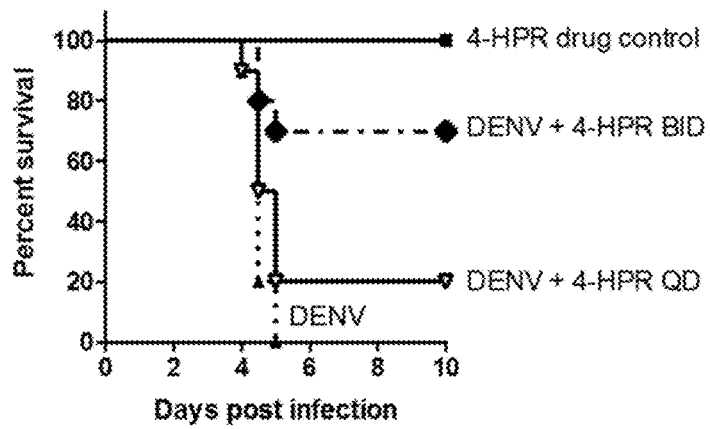

Mice have previously been used as an in vivo model for 4-HPR pharmacokinetics. To examine the effect of 4-HPR on DENV infection in vivo, a lethal mouse infection model, which uses a mouse adapted DENV-2 strain (S221), to infect Sv/129 mice deficient in type I and II interferon receptors (AG129) was used (Zellweger et al., 2010, Cell Host Microbe). Viral infection in this system is enhanced by intraperitoneal delivery of a sub-neutralizing concentration of 4G2 antibody 1 day prior to infection, resulting in peak viremia 3 days p.i. and death of infected mice by day 5. Here, mice were treated with 20 mg/kg of 4-HPR, administered orally at the time of infection, then once (QD) or twice (BID) daily for 5 consecutive days. Consistent with previous reports, infected, untreated mice all died by day 5 (FIG. 8B). Once daily treatment of mice with 4-HPR was sufficient to provide protection to 20% of mice, which recovered from the infectious challenge, whereas increasing the dose to 2 treatments daily, improved protection to 70% (7 of 10 mice recovered from the infectious challenge).

Figure 8C:
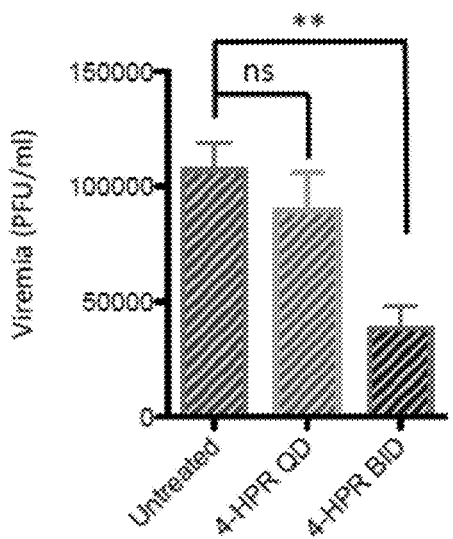

Analysis of plasma viral titres in mice 3 days p.i. revealed a small reduction in the average viral titre in the QD treatment group, while the BID treatment group was found to have an average viral titre 65% lower than that of the untreated group (**$p=0.002$, FIG. 8C), consistent with 4-HPR providing protection by lowering the amount of infectious DENV present in the infected and treated mice. Data are the mean+SEM. Statistical analysis (Student's t test) was performed using GraphPad Prism software (ns, not significant).

Example 9

4-HPR is Effective Against the Arboviruses Chikungunya Virus (CHIKV) and West Nile Virus (WNV)

HEK293T cells were treated with 5 µM 4-HPR or 4-MPR for 2 h, then infected with CHIKV for 1 h (MOI of 0.1) in the absence of compound (FIG. 9A). Alternatively, HEK293T cells were infected with CHIKV for 1 h (MOI of 0.1) without pre-treating the cells with compound (FIG. 9B). In both instances, virus inoculums were removed, then fresh medium containing the indicated compound was added (FIG. 9A and FIG. 9B). Infectious virus titres were determined by plaque assay 24 h p.i. Data are the mean+standard deviation of one experiment performed in duplicate wells, represented as plaque forming units per ml (PFU/ml).

Figure 9C:
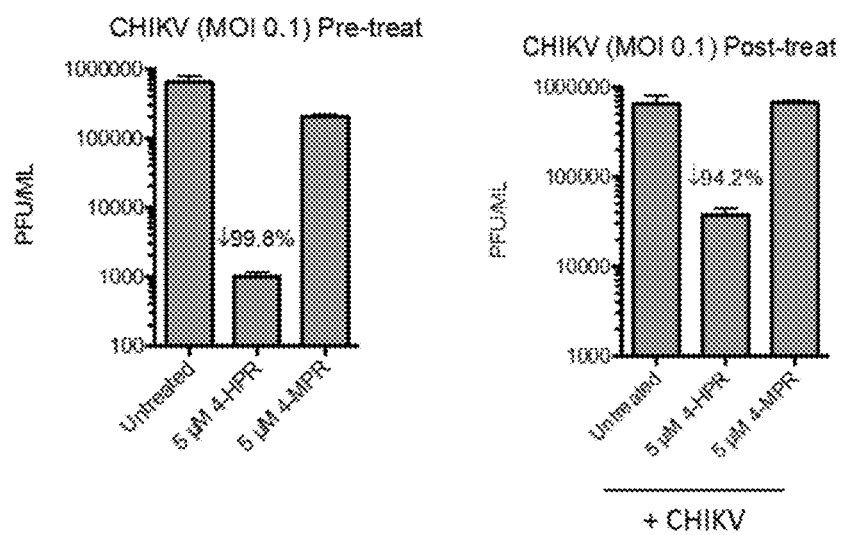
Figure 9C:
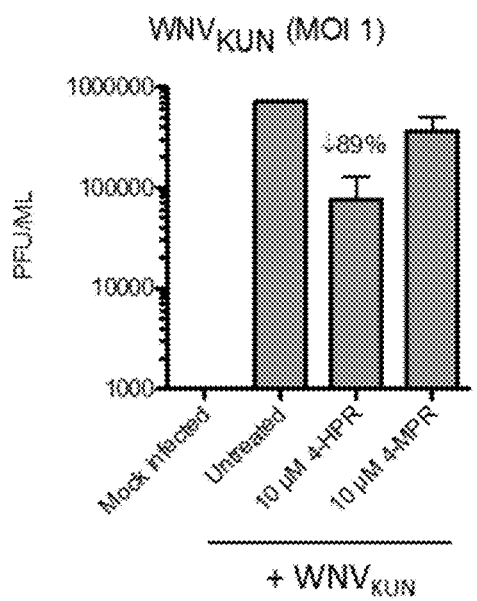

4-HPR (5 µM) was highly effective in restricting the production of infectious CHIKV, whether it was added to cells prior to infection or after infection. Compared to untreated controls, 4-HPR reduced the amount of infectious CHIKV produced by almost 100% in the cells that were pre-treated with compound, and by almost 95% in cells to which 4-HPR was added after infection. 4-MPR did not reduce CHIKV titres when added either prior to or after infection. Given that 4-HPR was effective in reducing CHIKV titres when added after virus attachment to cells, (FIG. 9B) it is likely that 4-HPR is effective at the level of RNA replication, similar to the mode of action of 4-HPR against DENV. 4-HPR also showed activity against the DENV-related flavivirus, West Nile virus, Kunjin strain (WNV$_{KUN}$; FIG. 9C), demonstrating an 89% reduction in infectious virus produced following a 4 h incubation of Vero cells with 10 µM 4-HPR at the time of infection. Again, 4-MPR was found to have no antiviral activity.

It will be understood that the invention disclosed and defined in this specification extends to all alternative combinations of two or more of the individual features mentioned or evident from the text or drawings. All of these different combinations constitute various alternative aspects of the invention.

REFERENCES

Caly L, Wagstaff K M, Jans D A. Subcellular trafficking of pathogens: targeting for therapeutics. Antiviral Res. 2012; 95, 202-6.

Clyde, K., Kyle, J. L., Harris, E. Recent advances in deciphering viral and host determinants of dengue virus replication and pathogenesis. J Virol. 2006; 80, 11418-31.

Formelli F., Cavadini, E., Luksch, R., Garaventa, A., Villani, M. G., Appierto, V., Persiani S. Pharmacokinetics of oral fenretinide in neuroblastoma patients: indications for optimal dose and dosing schedule also with respect to the active metabolite 4-oxo-fenretinide. Clin, Cancer Chemother Pharmacol. 2008; 62: 655-65.

Green S, Rothman A. Immunopathological mechanisms in Dengue and DHF. Curr Opin Infect Dis 2006; 19: 429-36.

Medin C L et al. DENV NS5 induces IL-8 transcription and secretion. J Virol 2005; 79: 11053.

Pryor M J et al. Nuclear localization of dengue virus nonstructural protein 5 through its importin α/β-recognized NLS is integral to viral infection. Traffic 2007; 8: 795-807.

Paradkar P N et al. UPR gene expression during antibody-dependent enhanced infection of cultured monocytes correlated with dengue disease severity. Bio Sci Rep 2010; 31: 221-230.

Wati S et al. Dengue (DV) replication in monocyte-derived macrophages is unaffected by TNF-α but DV infection induces altered responsiveness to TNF-α. J Virol 2007; 81: 10161-10171.

Zellweger R M et al. Enhanced infection of liver sinusoidal endothelial cells in a mouse model of antibody-induced severe dengue disease. Cell Host Microbe 2010; 7: 128-139.

The invention claimed is:

1. A method of preventing dengue virus (DENV) in a subject at risk of being exposed to DENV, comprising:
   administering a daily dose of N-(4-hydroxyphenyl) retinamide (4-HPR) to the subject of up to 4,000 mg/m$^2$/day during the period of time in which the subject is at risk of exposure,
   wherein the subject is not being administered an anti-viral agent other than 4-HPR.

2. The method of claim 1, further comprising administering the daily dose of 4-HPR of up to 4,000 mg/m$^2$/day for 1 to 5 days prior to being exposed to DENV.

3. The method of claim 1, further comprising administering the daily dose of 4-HPR of up to 4,000 mg/m$^2$/day for 1 to 14 days after being exposed to DENV.

4. The method of claim 1, wherein the subject has had a prior DENV infection.

5. The method of claim 1, wherein the dose administered is a single daily dose or divided daily doses.

6. A method of preventing dengue virus (DENV) in a subject at risk of being exposed to DENV, comprising:
   administering a daily dose of 4-HPR of up to 4,000 mg/m$^2$/day for 1 to 5 days prior to being exposed to DENV;
   administering a daily dose of N-(4-hydroxyphenyl) retinamide (4-HPR) to the subject of up to 4,000 mg/m$^2$/day during the period of time in which the subject is at risk of exposure; and
   administering a daily dose of 4-HPR of up to 4,000 mg/m$^2$/day for 1 to 14 days after being exposed to DENV
   wherein the subject is not being administered an anti-viral agent other than 4-HPR.

7. The method of claim 6, wherein the subject has had a prior DENV infection.

8. The method of claim 6, wherein the dose administered is a single daily dose or divided daily doses.

* * * * *